(12) United States Patent
Griffith

(10) Patent No.: US 7,212,866 B1
(45) Date of Patent: May 1, 2007

(54) IMPLANTABLE NEUROSTIMULATOR HAVING DATA REPEATER FOR LONG RANGE CONTROL AND DATA STREAMING

(75) Inventor: Glen A. Griffith, Newbury Park, CA (US)

(73) Assignee: Advanced Bionics Corporation, Valencia, CA (US)

( * ) Notice: Subject to any disclaimer, the term of this patent is extended or adjusted under 35 U.S.C. 154(b) by 414 days.

(21) Appl. No.: 10/763,843

(22) Filed: Jan. 23, 2004

Related U.S. Application Data

(60) Provisional application No. 60/447,304, filed on Feb. 12, 2003.

(51) Int. Cl.
*A61N 1/00* (2006.01)

(52) U.S. Cl. ............................ 607/60; 607/55; 607/57; 128/903

(58) Field of Classification Search .................. 607/60, 607/55–57; 128/903
See application file for complete search history.

(56) References Cited

U.S. PATENT DOCUMENTS 3,253,588 A    5/1966   Vuilleumier et al.
4,854,328 A    8/1989   Pollack
4,952,928 A    8/1990   Carroll et al.
4,958,645 A    9/1990   Cadell et al.
5,153,584 A   10/1992   Engira
5,383,915 A *  1/1995   Adams ......................... 607/60
5,603,726 A *  2/1997   Schulman et al. ............. 607/57
5,626,630 A *  5/1997   Markowitz et al. ........... 607/60
6,804,561 B2* 10/2004   Stover .......................... 607/60
7,110,822 B1*  9/2006   Palmer ......................... 607/57

* cited by examiner

*Primary Examiner*—Robert E. Pezzuto
*Assistant Examiner*—Brian T. Gedeon
(74) *Attorney, Agent, or Firm*—Bryant R. Gold; Victoria A. Poissant

(57) ABSTRACT

A repeater device allows a remote unit to control, program and/or monitor a medical implant device from a much further distance than has heretofore been possible. Such repeater device also facilitates transmitting other signals, i.e., other than control signals, to the medical implant device, such as, e.g., streaming audio, or other auxiliary input data. In one embodiment, the repeater device also allows status signals or sensed data originating within the medical implant device to be transmitted from the medical implant device through the repeater device to the remote unit, even though the remote unit may be located some distance, e.g., up to 200 feet, from the medical implant device. Such transmitted signals when received at the remote unit may be processed, analyzed, stored, monitored and/or displayed.

19 Claims, 3 Drawing Sheets

IMPLANTABLE NEUROSTIMULATOR HAVING DATA REPEATER FOR LONG RANGE CONTROL AND DATA STREAMING

The present application claims the benefit of U.S. Provisional Patent Application Ser. No. 60/447,304, filed Feb. 12, 2003, which application is incorporated herein by reference.

BACKGROUND OF THE INVENTION

The present invention relates to implantable neural stimulators, and more particularly to a way of increasing the distance from which an external remote control device is able to control and monitor the operation of a fully implantable neural system, such as a fully implantable cochlear implant system.

Representative cochlear implant systems are disclosed in the following U.S. patents, each of which is incorporated herein by reference: U.S. Pat. Nos. 5,824,022; 5,584,869; 5,603,726; and 6,219,580. A representative fully implantable cochlear implant system is disclosed in U.S. Pat. No. 6,308,101, also incorporated herein by reference.

A fully implantable cochlear implant system, or other fully implantable neural system, requires the use of a bi-directional telecommunications link, e.g., a radio frequency (RF) link, to communicate between the implant components and a remote control device for the purpose of setting the operating parameters of the implant system, and for monitoring its operation. The operating parameters of the implant system may include adjusting sensitivity, volume, program selection, ON/OFF control, and the like.

In a fully implanted cochlear implant system, such as that described in U.S. Pat. No. 6,308,101, the functions of the implant system are split between electronic circuitry contained in two separate housings: (1) an implantable speech processor (ISP) and (2) an implantable cochlear stimulator (ICS). The two housings are coupled to each other through a compact multi-turn coil through mutual inductance, as taught, e.g., in U.S. patent application Ser. No. 10/346,482, filed Jan. 17, 2003, now issued as U.S. Pat. No. 7,054,691 on May 30, 2006, which application and patent are assigned to the same assignee as the present application, and which application and patent are incorporated herein by reference. In such a system, the implantable speech processor (ISP) receives and transmits control signals through the multi-turn coil, using mutual inductance, by way of an imperceptible amount of energy which couples into the radiating modes. This link is therefore very limited in its transmission and reception range, which is typically only about 10–20 inches.

In the past, it has been necessary to hold the remote control device very close to an implantable device, .e.g., on or very near the skin surface above the location where the implant device is implanted. This is cumbersome and unsightly. In use, with the remote control device held on the skin above the implant location, it is usually difficult for the user to see the controls or displays on the remote control device when it must be held adjacent to the implant location.

In order to allow the remote control device to communicate with a fully implantable device from a farther distance, it has been necessary to increase the energy level of the signal transmitted to the implant device. Disadvantageously, such increase in transmitted signal strength only works in one direction, and increases the power consumption of the remote control device.

While radio repeater systems have been in use for many years for telephone, television and all forms of communications that use conventional rf communication links over large distances through the atmosphere or space, they have not, to applicant's knowledge, been adapted for use with medical implant systems where the signal must traverse through body tissue and fluids.

Therefore, it is evident that a need exists for improvements in the manner in which a remote control device communicates with a medical implant system, i.e., in the way that a remote control device communicates bi-directionally with a fully implanted device.

SUMMARY OF THE INVENTION

The present invention addresses the above and other needs by utilizing a small repeater device that allows a remote unit to control, program and/or monitor a medical implant device from a much further distance than has heretofore been possible. Such repeater device also facilitates transmitting other signals, i.e., other than control signals, to the medical implant device, such as, e.g., streaming audio, or other auxiliary input data. Moreover, the repeater device, in one embodiment, allows signals transmitted from the medical implant device, e.g., status signals or sensed data, to be transmitted to the remote unit, where such signals may be processed, analyzed, stored, monitored and/or displayed.

The repeater device (also referred to herein as simply the "repeater") included as part of the present invention operates at a different, i.e., higher, frequency than normally used by the implant device and its external controller/programmer, thereby allowing a physically small antenna to be used that couples well to the radiating modes. This feature greatly increases the transmission and reception ranges, since the radiating modes decrease in power as $1/r^2$, where "r" is the distance from the transmitter source, and whereas the ability to couple through mutual inductance decreases as $1/r^6$. Therefore, for the same available transmitting power, distances of several hundred feet are possible when a radiating mode is used.

One embodiment of the invention may be characterized as a repeater for use with an implantable neural system. The repeater comprises: (1) means for transmitting and receiving signals at a first frequency, wherein the first frequency is the frequency at which the implantable neural system is adapted to send and receive signals; (2) means for transmitting and receiving signals at a second frequency, wherein the second frequency is greater than the first frequency; (3) a first coil through which signals of the first frequency may be received from and sent to the implantable neural stimulator; (4) an antenna through which signals of the second frequency may be received from and sent to a remote unit, wherein the antenna is physically small; and (5) means for encoding and decoding signals of the first frequency to signals of the second frequency, and for encoding and decoding signals of the second frequency to signals of the first frequency, whereby signals of the second frequency received through the antenna may be converted to signals of the first frequency that are coupled through the first coil to the implantable neural stimulator, and whereby signals of the first frequency received through the first coil may be converted to signals of the second frequency that are transmitted through the antenna and coupled to the remote unit.

Another embodiment of the invention may be characterized as an implantable neural stimulator system that includes an implantable unit, a remote unit, and a repeater. The implantable unit includes an implanted receiving coil, circuitry for performing a specified function in accordance with programmed control signals, and means for receiving through the implanted receiving coil a first signal at a first frequency modulated with the programmed control signals. The remote unit includes means for generating the programmed control signals, a remote antenna, and transmitting means for transmitting through the remote antenna a radio frequency (RF) signal at a second frequency modulated with the programmed control signals, and wherein the second frequency is much greater than the first frequency. The repeater includes (1) means for transmitting signals at the first frequency, (2) means for receiving RF signals at the second frequency, (3) a first coil through which signals of the first frequency may be sent to the implantable neural stimulator, (4) an antenna through which signals of the second frequency may be received from the remote unit, wherein the antenna is physically small, (5) means for demodulating received signals of the second frequency in order to recover the programmed control signals therefrom, and (6) means for modulating the signal of the first frequency with the programmed control signals and presenting the modulated first frequency signal to the transmitting means. Using such a system allows signals of the second frequency modulated with the programmed control signals and received through the antenna from the remote unit to be converted to signals of the first frequency modulated with the programmed control signals that are coupled through the first coil to the implantable neural stimulator. The benefit of using such a system is that the programmed control signals, generated by the remote unit, may be transferred into the implantable neural stimulator by way of the repeater.

Advantageously, although the repeater of the present invention must be physically close to the implantable neural stimulator, i.e., directly over or near the location under the skin where the implantable neural stimulator is implanted, the remote unit may be physically far, e.g, up to 200 feet or more from the repeater.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

A preferred neurostimulator system with which the present invention is used is a cochlear implant system, which system is designed to allow a user who is profoundly deaf to perceive audio sounds (i.e., hear) through direct electrical stimulation of the auditory nerve. Thus, a preferred embodiment of the invention described below relates to a cochlear implant system. However, it should be emphasized that the invention—a repeater device used with a medical implant device—need not be limited to use with a cochlear implant system. Rather, the invention may be used with any type of implantable neurostimulator system where there is a need for non-invasive control, programmability or monitoring of a medical implant device from a distance more than a few inches from the location where the medical implant device is implanted.

Figure 1:
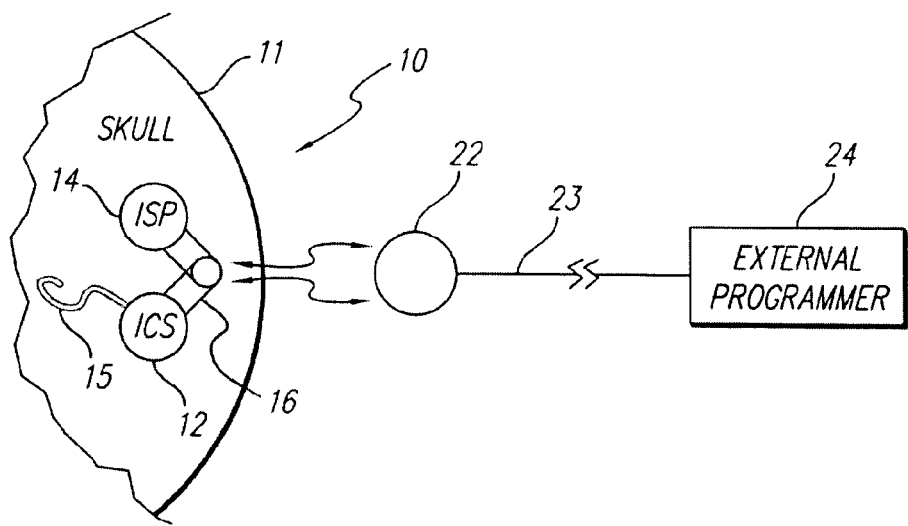
FIG. 1 illustrates one type of fully implantable system and an external remote control device used therewith.

FIG. 1 shows one type of a fully implantable system 10 for stimulating the cochlea. The fully implantable system includes an implantable cochlear stimulator (ICS) 12 and an implantable speech processor (ISP) 14. The ISP 14 and ICS 12 are mutually coupled through aligned and overlapping coils 16. The ICS 12, ISP 14 and overlapping coils 16 are all implanted within the skull of a patient 11. An electrode array 15 is connected to the ICS 12, and has an array of tiny electrodes adapted for insertion into the patient's cochlea.

The coils 16 also are positioned so that an external coil 22, included, e.g., as part of a head piece, may be inductively coupled therewith. The external coil 22 is connected by way of a flexible cable 23 to an external programmer 24, or other suitable remote control device. The external programmer 24, or other remote control device, sends control signals to the implantable system 10 through the mutually coupled coils 22 and 16. The implantable system 10 likewise sends status signals through the coupled coils 22 and 16 to the external programmer 24.

Because the external coil 22 is adapted to be mutually coupled to the implanted coils 16 through mutual inductance, it is necessary that the external coil 22 be relatively close to the implanted coils 16 in order for proper mutual inductance coupling to occur. The communication works best when the external coil 22 is aligned with implanted coils 16 and is resting on the skin of the patient immediately above the location at which the implanted coils 16 are located. In practice, the external coil (which may be part of a headpiece) must be within just a few inches, e.g., 2–20 inches, of the implanted coils in order for communication to occur.

In operation, the external programmer 24 generates control and programming signals that are coupled through the coils 22 and 16 to the ISP 14. The ISP 14 processes the signals and sends appropriate control signals to the ICS 12 that cause it to generate electrical stimuli that are delivered through the tiny electrode array 15 to the auditory nerve in the cochlea. Status signals may be send from the ICS 12 and ISP 14 through the coils 16 and 22 to the external programmer 24, where such status signals may be displayed and/or saved.

Figure 1A:
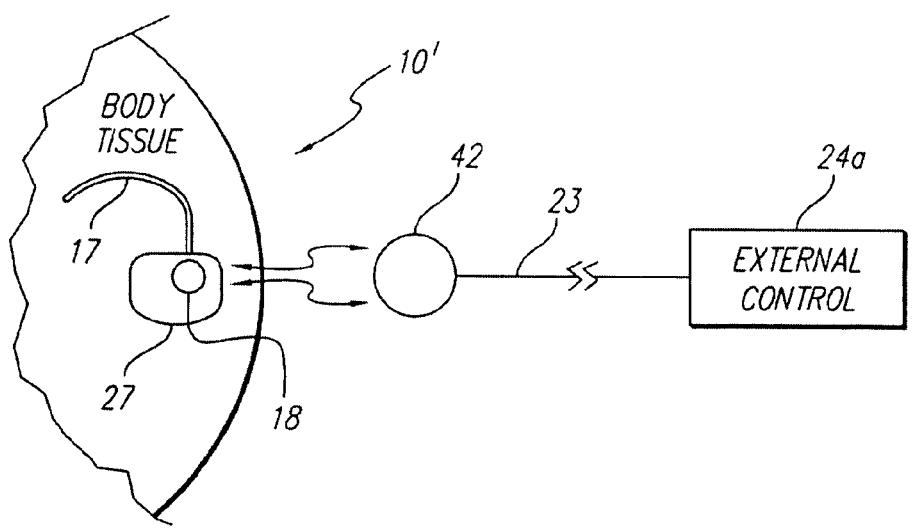
FIG. 1A illustrates another type of a fully implantable system and an external remote control device used therewith.

Another type of fully implantable system 10' that may be used with the invention is shown in FIG. 1A. The fully implantable system 10' shown in FIG. 1A includes a one-piece housing or case 27 in which electrical circuitry that performs the function of an implantable speech processor (ISP) and an implantable pulse generator (IPG) is housed, along with a suitable power source. A coil 18 is included in or on the case 27 through which mutual inductive coupling may occur with an external coil 42. The external coil 42 is coupled through a wire or cable 23 with an external control device 24a, such as an external programmer. An electrode array 17 is attached to the one-piece housing 27 and has tiny electrode contacts thereon through which electrical stimulation may be applied to selected body tissue. The electrical circuitry contained within the housing or case 27 generates electrical stimuli that are selectively applied to the body tissue through the electrode contacts on the electrode array 17 in accordance with programmed control signals that are loaded into the electrical circuitry from the external control device 24a.

One exemplary embodiment of a fully implantable system of the type shown in FIG. 1A is a one-piece fully implantable cochlear stimulation system, in which the electrode array 17 is adapted for insertion into the cochlea of a user. However, it should be understood that the invention is not limited for use with an implantable cochlear stimulation system. Any type of implantable neural stimulation system that requires occasional or periodic external communications with an external control device, e.g., for the purpose of adjusting the intensity of stimuli parameters, programming or monitoring, may be used with the invention.

Figure 2:
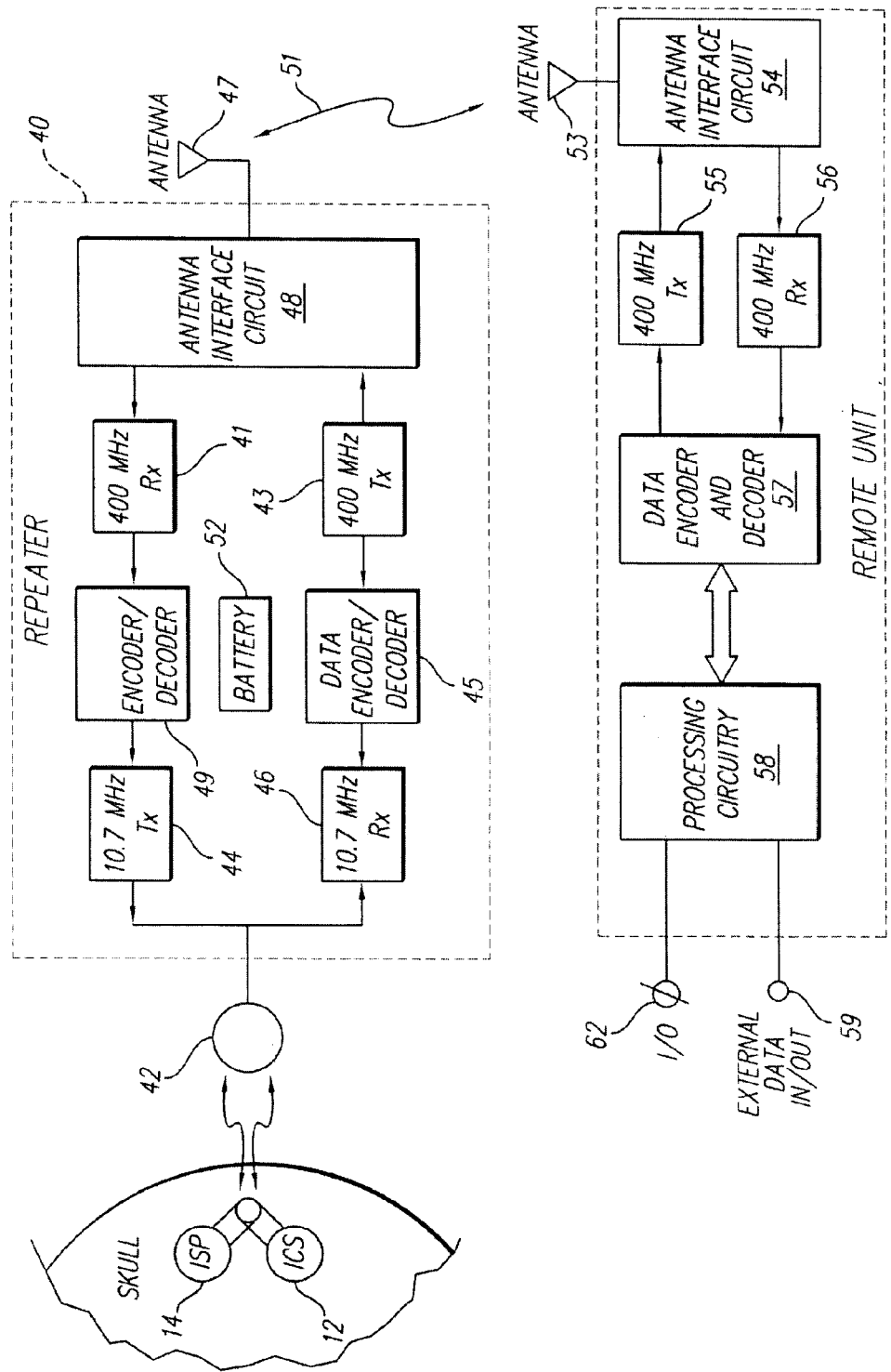
FIG. 2 shows a block diagram of the invention, and shows how it interfaces with an implantable system and a remote unit.

FIG. 2 shows a block diagram of a repeater 40 used with a fully implantable system 10 or 10' in accordance with the present invention. The repeater 40 accesses the half-duplex capability of the ICS 12, and under its protocol control is slaved to transmit or receive. The repeater has both a 10.7 MHz transmitter 44 and a 10.7 MHz receiver 46 attached to its coil 42. The receiver recovers the digitized message in a data encoder/decoder 45, and applies it to an outgoing transmitter 43, which for purposes of discussion operates at 400 MHz.

The 400 MHz transmit signal is applied through a suitable antenna interface circuit 48 to an antenna 47, from which it radiates as a transmitted RF signal 51. Because the transmit frequency is relatively high, the antenna 47 may be physically small. This is an important feature, because it allows the repeater 40, including its antenna 47, to be placed near the implanted coils 16, yet remain relatively inconspicuous.

The antenna interface circuit 48 may be of any suitable design as is known in the RF art. The function of the RF interface circuit is, inter alia, to allow high frequency RF signals of a specified frequency, e.g., 400 MHz, to be simultaneously received and transmitted through antenna 47. The signals received through antenna 47 are directed to the receiver 41; while the signals transmitted through antenna 47 are received from transmitter 43. One of the primary functions of such an interface circuit is to match impedances between the antenna 47 and the respective receiver or transmitter circuit. One type of antenna interface circuit comprises a simple air core transformer, tuned to the appropriate frequency using an LC circuit made from capacitors and the inductance of the air core transformer, having a first (primary) winding connected to the antenna 47, a second (1st secondary) winding connected to the receiver 41, and a third (2nd secondary) winding connected to the transmitter 43. Other types of antenna interface circuits known in the art may also be used.

The repeater 40 shown in FIG. 2 operates as a frequency diplexer. That is, the repeater 40 is able to both transmit and receive signals simultaneously. To that end, a 400 MHz Receiver 41 is configured to receive signals from the antenna 47 at the same time that the 400 MHz transmitter 43 is transmitting signals through the antenna 47. (In actuality, the frequency of the signal that is transmitted by the transmitter 43 will be slightly different than the frequency received by the receiver 41. That is, the transmit frequency may be, e.g., 400 MHz, while the receive frequency may be, e.g., 410 MHz.) A decoder/encoder circuit 49 extracts the data from the received signal (the signal received through the receiver 41) and formats it, as needed, for transmission at a second, lower, frequency, e.g., 10.7 MHz, by a transmitter circuit 44. The transmitter circuit 44 sends the signal to the external coil 42, from which point it is coupled into the internal coils 16 for use by the Implanted system 10 or 10'.

A suitable battery 52, or other power source, is carried within the repeater 40. This battery is easy replaced or recharged, when depleted.

Thus it is seen that the repeater 40 receives and transmits signals from and to the implanted system 10 (or 10') and receives and transmits signals from and to a remote unit 50. In essence, the repeater functions as a pass-through device. Signals received from the implanted system at one frequency are decoded and encoded and re-transmitted at another frequency to the remote unit 50. Similarly, signals received from the remote unit at one frequency are decoded and encoded and re-transmitted at another frequency to the implanted system 10 (or 10'). Signals sent to and received from the remote unit 50 may be, e.g., around 400 MHz. Signals sent to and received from the implanted system 10 (or 10') may be, e.g., around 10.7 MHz.

The signals passing through antenna 47, whether being transmitted or received, must have a frequency that is a relatively high frequency. Such relatively high frequency, e.g., 400 MHz, allows the signals to radiate over a relatively far distance, e.g., 20–200 feet. This allows a remote unit 50, having an antenna 53, to receive and send such signals, even though the remote unit may be as far as 200 feet away from the repeater 40. In contrast, the relatively lower frequency signals that are sent and received through the repeater coil 42 and the implanted coils 16 or 18 allow coupling between the coils over a relatively short distance, e.g., only a few inches, such as 4 or 5 inches or less.

The remote unit 50, which for most applications functions as a remote control unit, allows a remote user to program and monitor the operation of the implantable system 10. To that end, the remote unit includes, in addition to a suitable antenna 53, an antenna interface circuit that couples with a transmitter 55 and a receiver 56. Such antenna interface circuit 54 may be as described above in connection with the repeater antenna interface circuit 48. A suitable decoder/ encoder circuit 57, e.g., a modulator/demodulator circuit, connects the receiver 55 and transmitter 56 with a suitable processor circuit 58. The processor circuit 58, which may be realized using a conventional microprocessor chip with memory, performs whatever control or processing functions have been programmed or that are selected. An I/O port 62 allows a user to send data to the processor, i.e., through push buttons, knobs, and/or a keyboard. An external computer, e.g., a notebook-sized computer, may similarly interface through the external data port 62 with the remote unit, which in turn is linked via the RF signals 51 and the repeater 40, with the implantable system 10. An external data port 59 allows external data, e.g., external audio streaming data, to be input into the remote unit 50 for transmission to the implantable system. Alternatively, data sent from the implantable system 10 may be received through the external data port 59 for recording and/or analysis.

Figures 3A, 3B, 3C:
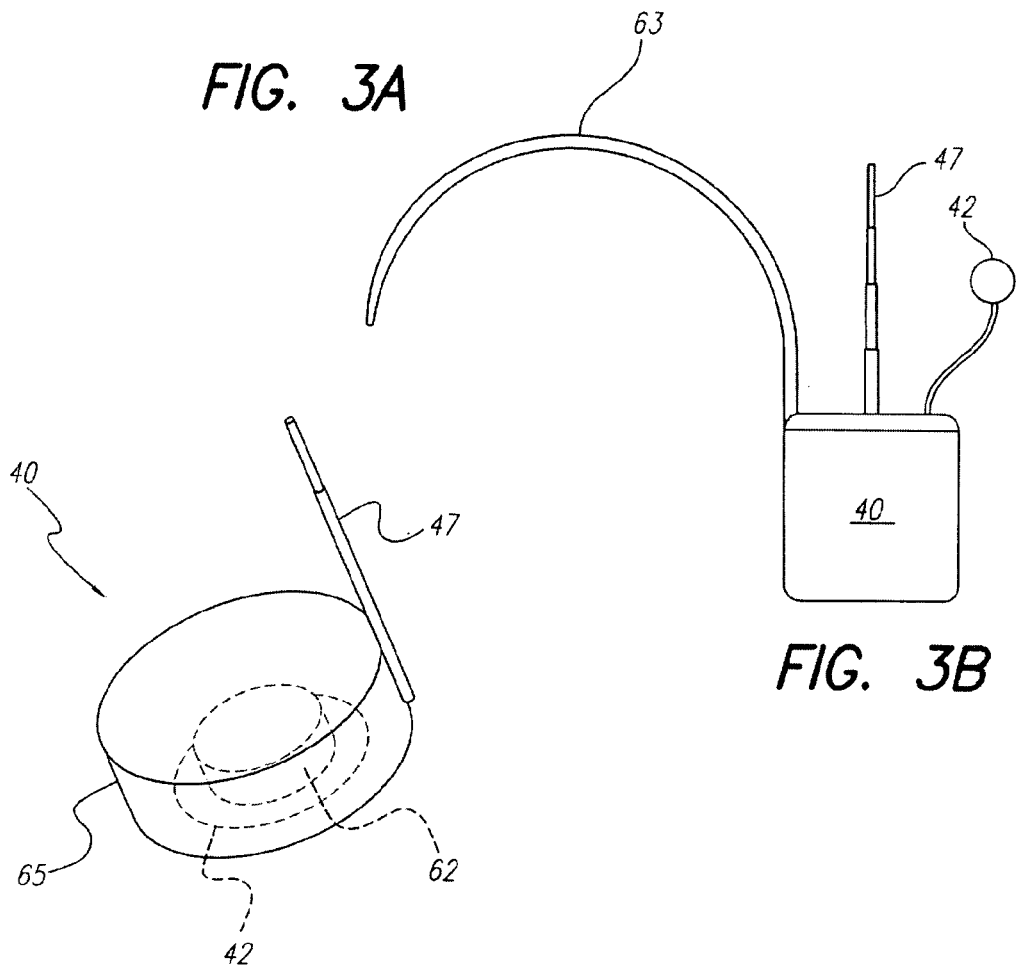
FIG. 3A depicts one technique for holding the repeater on an ear hook.
FIG. 3B depicts a technique for holding the repeater on a head strap or headphone-type device.
FIG. 3C depicts another embodiment of the repeater adapted to be held in place by a magnet.

FIG. 3A shows the repeater 40 of the present invention attached to an ear hook 61. Use of the ear hook 61 places the repeater 40, and more particularly its coil 42, in close proximity to the coils 16 or 18 of the implantable systems 10 or 10'. The antenna 47 may telescope up from the repeater 40 a short distance, if needed. Generally, however, the antenna 47 need not be very long. In some embodiments, the antenna 47 may simply be a flexible wire that hangs from the repeater 40.

The repeater 40 may also be attached to a small headphone type strap 63, or a strap 63 adapted to fit over the head like a headphone, as shown in FIG. 3B. Thus, it is seen that the repeater 40 may be used in many configurations and arrangements. A larger battery is possible with the headphone strap type arrangement, although battery life is not an essential feature of the invention because the battery can be readily changed or replaced in the non-implanted repeater 40.

The repeater 40 may further be housed within a disk-shaped (or other shaped) housing 65 having a magnet 62 located therein as shown in FIG. 3C. The magnet 62 is adapted to magnetically couple with a magnet located within the implantable system 10 or 10', to thereby hold the housing 65, including the external coil 42 which is located near or on a surface of the housing 65, in place over the implanted coils 16 or 18. Antenna 47 extends outwardly from the housing 65, either as a stiff member, e.g., a rod, or as a flexible member, e.g., a hanging wire.

Still with reference to FIG. 3C, when a user of the implantable system 10 or 10' needs to monitor or control or adjust the implantable system 10 or 10', the user simply temporarily places the housing 65 of the repeater 40 over the location where the implanted coils and magnet reside, and magnetic forces then hold housing 65 in place over the implanted coils in good alignment therewith. The user then operates the remote control unit 50, e.g., held in his or her hand, and communications with the implantable system occur through the repeater 40. When all needed communications with the implantable system have occurred, the user turns off the remote control unit 50 and the repeater 40 may be removed and placed in the user's pocket or purse or other suitable location.

For the embodiments of the repeater shown in FIGS. 3A and 3B, the repeater may similarly be temporarily placed in position for operation only when communications with the implanted system are needed. When such communications are not needed, then the repeater may be removed. Alternatively, if the user desires, the repeater may be carried on the ear hook (FIG. 3A) or the headphone type device (FIG. 3B), even when communications are not needed.

Advantageously, the Repeater arrangement shown in FIG. 2 may be operated as an FIS FM system for FM assisted hearing usage.

Further, additional ports may also be used that allow the user to access auxiliary inputs and outputs for other applications, such as a cordless phone, or microphone, or a cordless intercom system.

While the invention herein disclosed has been described by means of specific embodiments and applications thereof, numerous modifications and variations could be made thereto by those skilled in the art without departing from the scope of the invention set forth in the claims.

What is claimed is:

1. A repeater for use with an implantable neural system, the repeater comprising:

means for transmitting and receiving signals at a first frequency, wherein the first frequency is the frequency at which the implantable neural system is adapted to send and receive signals;

means for transmitting and receiving signals at a second frequency, wherein the second frequency is greater than the first frequency;

a first coil (42) through which signals of the first frequency may be received from and sent to the implantable neural stimulator;

an antenna (47) through which signals of the second frequency may be received from and sent to a remote unit, wherein the antenna is physically small;

an antenna interface circuit (48), and wherein the antenna (47) is coupled to a second receiver circuit (41) and a second transmitter circuit (43) through the antenna interface circuit (48); and holding means for temporarily holding the repeater and the first coil (42) in alignment with the implantable neural system;

wherein the means for transmitting and receiving signals at the first frequency comprises a first receiver circuit (46) and a first transmitter circuit (44), each of which is coupled to the first coil (42);

wherein the means for transmitting and receiving signals at the second frequency comprises the second receiver circuit (41) and the second transmitter circuit (43), each of which is coupled to the antenna (47); and wherein the holding means comprises an ear hook adapted to fit over a user's ear, and wherein the repeater is mounted on the ear hook.

2. The repeater of claim 1 wherein the first frequency is about 10.7 MHz.

3. The repeater of claim 1 wherein the second frequency is about 400 MHz.

4. A repeater for use with an implantable neural system, the repeater comprising:

means for transmitting and receiving signals at a first frequency, wherein the first frequency is the frequency at which the implantable neural system is adapted to send and receive signals;

means for transmitting and receiving signals at a second frequency, wherein the second frequency is greater than the first frequency;

a first coil (42) through which signals of the first frequency may be received from and sent to the implantable neural stimulator;

an antenna (47) through which signals of the second frequency may be received from and sent to a remote unit, wherein the antenna is physically small;

an antenna interface circuit (48), and wherein the antenna (47) is coupled to a second receiver circuit (41) and a second transmitter circuit (43) through the antenna interface circuit (48); and holding means for temporarily holding the repeater and the first coil (42) in alignment with the implantable neural system;

wherein the means for transmitting and receiving signals at the first frequency comprises a first receiver circuit (46) and a first transmitter circuit (44), each of which is coupled to the first coil (42);

wherein the means for transmitting and receiving signals at the second frequency comprises the second receiver circuit (41) and the second transmitter circuit (43), each of which is coupled to the antenna (47); and wherein the holding means comprises a housing having a magnet therein, and wherein the magnet is adapted to magnetically engage with a magnetic member of the implantable neural system and to thereby hold the housing in place over the implantable neural system.

5. The repeater of claim 4 wherein the first frequency is about 10.7 MHz and the second frequency is about 400 MHz.

6. An implantable neural stimulator system comprising:
an implantable unit comprising an implanted receiving coil, circuitry for performing a specified function in accordance with programmed control signals, and means for receiving a first signal at a first frequency modulated with said programmed control signals through said implanted receiving coil;
a remote unit comprising means for generating the programmed control signals, a remote antenna, and transmitting means for transmitting an RF signal through the remote antenna at a second frequency modulated with the programmed control signals, wherein the second frequency is much greater than the first frequency;
a repeater comprising
means for transmitting signals at the first frequency,
means for receiving RF signals at the second frequency,
a first coil (42) through which signals of the first frequency may be sent to the implantable unit,
an antenna (47) through which signals of the second frequency may be received from the remote unit, wherein the antenna is physically small, and
means for demodulating received signals of the second frequency in order to recover the programmed control signals therefrom, and means for modulating the signal of the first frequency with the programmed control signals and presenting the modulated first frequency signal to the transmitting means,
whereby signals of the second frequency modulated with the programmed control signals and received through the antenna from the remote unit may be converted to signals of the first frequency modulated with the programmed control signals that are coupled through the first coil to the implantable unit;
whereby the programmed control signals, generated by the remote unit, may be transferred into the implantable unit by way of the repeater, and
holding means for temporarily holding the repeater and the first coil (42) in alignment with the implantable unit, wherein the holding means comprises a housing having a magnet therein, and wherein the magnet is adapted to magnetically engage with a magnetic member of the implantable unit and to thereby hold the housing in place over the implantable unit.

7. The implantable neural stimulator system of claim 6 wherein the first frequency of the signal sent to the implantable neural stimulator through the first coil is about 10.7 MHz, and wherein the second frequency of the RF signal transmitted by the remote unit is about 400 MHz.

8. The implantable neural stimulator system of claim 7 wherein the range over which a signal of the first frequency may be transmitted from the repeater to the implantable neural stimulator is less than about 5 inches.

9. The implantable neural stimulator system of claim 7 wherein the range over which a signal of the second frequency may be transmitted from the remote unit to the repeater is about 200 feet.

10. The implantable neural stimulator system of claim 6 wherein the remote unit further includes an input port through which an externally-generated signal may be input and transmitted to the implantable neural stimulator through the repeater.

11. An implantable neural stimulator system comprising:
an implantable unit comprising an implanted coil, circuitry for performing a specified function in accordance with programmed control signals, means for sensing status information relating to the operation of the implantable unit; means for receiving a first signal of a first frequency modulated with said programmed control signals through said implanted coil, and means for transmitting a signal of the first frequency modulated with the status information through said implanted coil;
a remote unit comprising means for generating the programmed control signals, a remote antenna, transmitting means for transmitting an RF signal through the remote antenna at a second frequency modulated with the programmed control signals, receiver means for receiving an RF signal through the remote antenna at said second frequency modulated with the status information, and means for processing and displaying relevant information derived from the status information and programmed control signals, wherein the second frequency is much greater than the first frequency;
a repeater comprising
means for transmitting and receiving signals at the first frequency,
means for transmitting and receiving signals at the second frequency,
a first coil through which signals of the first frequency may be received from and sent to the implantable unit,
an antenna through which signals of the second frequency may be received from and sent to a remote unit, and
means for encoding and decoding signals of the first frequency to signals of the second frequency, and for encoding and decoding signals of the second frequency to the signals of the first frequency, whereby signals of the second frequency received through the antenna may be converted to signals of the first frequency that are coupled through the first coil to the implantable unit, and whereby signals of the first frequency received through the first coil may be converted to signals of the second frequency that are transmitted through the antenna and coupled to the remote unit, and
holding means for temporarily holding the repeater and the first coil in alignment with the implantable unit, wherein the holding means comprises a housing having a magnet therein, and wherein the magnet is adapted to magnetically engage with a magnetic member of the implantable unit and to thereby hold the housing in place over the implantable unit.

12. The implantable neural stimulation system of claim 11 wherein the first frequency comprises a frequency of about 10.7 MHz, and wherein the second frequency comprises a frequency of about 400 MHz.

13. The implantable neural stimulation system of claim 12 wherein signals received from the remote unit through the repeater antenna do not have exactly the same frequency as signals transmitted from the repeater through the repeater antenna to the remote unit.

14. The implantable neural stimulation system of claim 13 wherein signals received from the remote unit through the repeater antenna have a frequency that is 410 MHz, and signals transmitted from the repeater through the repeater antenna to the remote unit have a frequency that is about 400 MHz.

15. The implantable neural stimulator system of claim 11 wherein the range over which a signal of the first frequency may be transmitted from the repeater to the implantable neural stimulator is less than about 5 inches, and wherein the range over which a signal of the second frequency may be transmitted from the remote unit to the repeater is greater than 20 feet.

16. An implantable neural stimulator system comprising:
an implantable unit comprising an implanted receiving coil, circuitry for performing a specified function in accordance with programmed control signals, and means for receiving a first signal at a first frequency modulated with said programmed control signals through said implanted receiving coil;
a remote unit comprising means for generating the programmed control signals, a remote antenna, and transmitting means for transmitting an RF signal through the remote antenna at a second frequency modulated with the programmed control signals, wherein the second frequency is much greater than the first frequency;
a repeater comprising
means for transmitting signals at the first frequency,
means for receiving RF signals at the second frequency,
a first coil (42) through which signals of the first frequency may be sent to the implantable unit,
an antenna (47) through which signals of the second frequency may be received from the remote unit, wherein the antenna is physically small, and
means for demodulating received signals of the second frequency in order to recover the programmed control signals therefrom, and means for modulating the signal of the first frequency with the programmed control signals and presenting the modulated first frequency signal to the transmitting means,
whereby signals of the second frequency modulated with the programmed control signals and received through the antenna from the remote unit may be converted to signals of the first frequency modulated with the programmed control signals that are coupled through the first coil to the implantable unit;
whereby the programmed control signals, generated by the remote unit, may be transferred into the implantable unit by way of the repeater, and
holding means for temporarily holding the repeater and the first coil (42) in alignment with the implantable unit, wherein the holding means comprises an ear hook adapted to fit over a user's ear, and wherein the repeater is mounted on the ear hook.

17. The implantable neural stimulation system of claim 16 wherein the first frequency comprises a frequency of about 10.7 MHz, and wherein the second frequency comprises a frequency of about 400 MHz.

18. An implantable neural stimulator system comprising:
an implantable unit comprising an implanted coil, circuitry for performing a specified function in accordance with programmed control signals, means for sensing status information relating to the operation of the implantable unit; means for receiving a first signal of a first frequency modulated with said programmed control signals through said implanted coil, and means for transmitting a signal of the first frequency modulated with the status information through said implanted coil;
a remote unit comprising means for generating the programmed control signals, a remote antenna, transmitting means for transmitting an RF signal through the remote antenna at a second frequency modulated with the programmed control signals, receiver means for receiving an RF signal through the remote antenna at said second frequency modulated with the status information, and means for processing and displaying relevant information derived from the status information and programmed control signals, wherein the second frequency is much greater than the first frequency;
a repeater comprising
means for transmitting and receiving signals at the first frequency,
means for transmitting and receiving signals at the second frequency,
a first coil through which signals of the first frequency may be received from and sent to the implantable unit,
an antenna through which signals of the second frequency may be received from and sent to a remote unit, and
means for encoding and decoding signals of the first frequency to signals of the second frequency, and for encoding and decoding signals of the second frequency to the signals of the first frequency, whereby signals of the second frequency received through the antenna may be converted to signals of the first frequency that are coupled through the first coil to the implantable unit, and whereby signals of the first frequency received through the first coil may be converted to signals of the second frequency that are transmitted through the antenna and coupled to the remote unit, and
holding means for temporarily holding the repeater and the first coil in alignment with the implantable unit, wherein the holding means comprises an ear hook adapted to fit over a user's ear, and wherein the repeater is mounted on the ear hook.

19. The implantable neural stimulation system of claim 18 wherein the first frequency comprises a frequency of about 10.7 MHz, and wherein the second frequency comprises a frequency of about 400 MHz.

* * * * *